United States Patent [19]

Reifschneider

[11] Patent Number: 4,474,958

[45] Date of Patent: Oct. 2, 1984

[54] 2-ALKYL-5-HALOPYRIMIDINES

[75] Inventor: Walter Reifschneider, Walnut Creek, Calif.

[73] Assignee: The Dow Chemical Company, Midland, Mich.

[21] Appl. No.: 389,638

[22] Filed: Jun. 18, 1982

[51] Int. Cl.$^3$ ............................................ C07D 239/30
[52] U.S. Cl. ...................................... 544/334; 544/243
[58] Field of Search ........................................ 544/334

[56] References Cited

U.S. PATENT DOCUMENTS

| | | | |
|---|---|---|---|
| 2,937,171 | 5/1960 | Smith | 544/334 |
| 3,402,193 | 9/1968 | Hagemeyer et al. | 260/453 |
| 4,012,506 | 3/1977 | Balke et al. | 544/243 |
| 4,053,473 | 10/1977 | Durant et al. | 544/334 |
| 4,127,652 | 11/1978 | Maurer et al. | 544/243 |
| 4,379,930 | 4/1983 | Pews | 544/298 |

OTHER PUBLICATIONS

Brown, *The Pyrimidines, Supplement I,* 1970, Wiley-Interscience, New York, pp. 119–122; 148.

Buděšínsk, "Chemical Abstracts", vol. 44, 1950, Col. 1516e.
Geerts, et al., "Chemical Abstracts", vol. 83, 1975, Col. 42517t.
Rasmussen, et al., "Chemical Abstracts", vol. 90, 1979, Col. 72140b.
Brown, et al., "J. Chem. Soc.", 1962, pp. 4039–4045.
Jutz, et al., "Chem. Ber.", vol. 102, 1969, pp. 2301–2318.
Kucera, et al., "Collect. Czech. Chem. Comm.", vol. 32, 1967, pp. 1704–1711.
Oostveen, et al., "Rec. Trav. Chim.", Pays–bas 95, 1976, pp. 209–211.

*Primary Examiner*—Glennon H. Hollrah
*Assistant Examiner*—James H. Turnipseed

[57] ABSTRACT

Novel 2-alkyl-5-halopyrimidines, e.g., 5-chloro-2-(1,1-dimethylethyl)pyrimidine, which are useful as intermediates in the preparation of, e.g., O,O-diethyl O-(2-(1,1-dimethylethyl)-5-pyrimidinyl) phosphorothioate which is useful as an insecticide against corn rootworm and cutworm.

5 Claims, No Drawings

2-ALKYL-5-HALOPYRIMIDINES

BACKGROUND OF THE INVENTION

This invention relates to novel 2-alkyl-5-halopyrimidines, a process for producing them and their use as intermediates in making insecticides useful for the control of insects such as corn rootworm and cutworm.

The preparation of 5-halogenopyrimidine is described in "Heterocyclic Compounds, The Pyrimidines, Supplement I" (1970) Wiley-Interscience, pages 119 ff. The compounds 5-chloro- and 5-bromo-2-methylpyrimidine and 5-chloro- and 5-bromopyrimidine are known (CA 44, 1516e), as well as the compounds 5-chloro-4-tert-butylpyrimidine and 5-bromo-4-tert-butylpyrimidine (CA 90, 72140b and 83, 42517t).

SUMMARY OF THE INVENTION

The novel compounds of this invention are 2-alkyl-5-halopyrimidines having the formula:

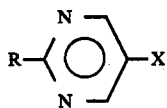

wherein R is cyclopropyl, isopropyl or t-butyl and X is Cl or Br.

These compounds are advantageously employed as intermediates in the preparation of 0-alkyl-0-[pyrimidin(5)yl]-(thiono)(thiol)-phosphoric (phosphonic) acid esters or ester-amides having exceptional insecticidal activity by the processes described in U.S. Pat. No. 4,127,652 or copending application Ser. No. 928,665, filed July 28, 1978. For such processes, the halopyrimidines are first hydrolyzed as taught in Supplement I of "The Pyrimidines", Interscience (1970), page 148 or in copending application Ser. No. 301,686, filed Sept. 14, 1981 now U.S. Pat. No. 4,379,930 issued Apr. 12, 1983.

The invention is further illustrated by the following examples.

EXAMPLE 1

-5-Chloro-2-cyclopropylpyrimidine

To a stirred mixture of 15.5 g of cyclopropanecarboximidamide monohydrochloride, 30.9 g of N-(2-chloro-3-(dimethylamino)2-propylidene)-N-methylmethanaminium perchlorate and 50 ml of methanol was added dropwise, a sodium methoxide solution prepared from 8.2 g of sodium and 150 ml of methanol. After the addition was complete, the mixture was heated under reflux for approximately three hours. The reaction mixture was concentrated under vacuum and the distillate which contained some product was saved. The residue was taken up in ether, washed with water, saturated in sodium chloride solution and dried over anhydrous sodium sulfate. The ether solution was combined with the distillate and the solvents were removed by distillation using a 50 cm vacuum jacketed Vigreux column leaving 16 g (87 percent of theoretical) of product. The material was distilled in a Kugelrohr (bath temperature 45° C., pressure 0.1 mm) to give a colorless oil which solidified on standing. Recrystallization from hexane gave white crystals, m.p. 37°–38° C.

Analysis: Found: C, 54.10; H, 4.88; N, 18.25.

Calculated for $C_7H_7ClN_2$: C, 54.38; H, 4.56; N, 18.12.

EXAMPLE 2

-5-Chloro-2-(1-methylethyl)pyrimidine)

A Vilsmeier reagent was prepared below 0° C. from 610 ml of dimethylformamide and 190 g of phosgene and 60 g of chloroacetic acid were added. The mixture was then carefully warmed to 70° C., kept at this temperature for two hours and was then heated to 85° C. for another two hours. The excess dimethylformamide was removed as far as practical under vacuum. The residue was taken up in 300 ml of methanol, 70 g of 2-methylpropanimidamide monohydrochloride was added and to the resulting mixture 900 ml of 25 percent sodium methoxide in methanol were added dropwise. After the addition was complete, the mixture was heated under reflux for three hours. The salts were removed by filtration and the filtrate concentrated under vacuum. The residual oil was triturated with water and the mixture extracted several times with ether. The ether extract was washed with saturated sodium chloride solution and dried over anhydrous sodium sulfate. The ether was removed under vacuum and the residual oil fractionated on a small Vigreux column, yielding 20 g (22 percent of theoretical) of a colorless oil RI (25° C.)=1.4930; b.p. 80° C. at 12 mm.

Analysis: Found: C, 53.58; H, 6.02; N, 17.74.

Calculated for $C_7H_9ClN_2$: C, 53.68; H, 5.79; N, 17.89.

EXAMPLE 3

-5-Chloro-2-(1,1-dimethylethyl)pyrimidine

To a stirred mixture of 80 g of N-(2-chloro-3-(dimethylamino)-2-propylidene)-N-methylmethanaminium perchlorate, 46 g of 2,2-dimethylpropanimidamide monohydrochloride and 100 ml of methanol was added dropwise a sodium methoxide solution, prepared from 21 g of sodium and 250 ml of methanol. After the addition was complete, the mixture was heated under reflux for two hours. The reaction mixture was concentrated under vacuum and the distillate which contained some product was saved. The residue was taken up in ether, washed twice with water, once with saturated sodium chloride solution and dried over anhydrous sodium sulfate. The ether extract was combined with the distillate and the solvents were removed by distillation, using a Vigreux column. The residue was then fractionated in a small Vigreux column and 42 g (80 percent of theoretical) of colorless oil were collected at 82° C. and 18 mm RI (25° C.)=1.4944. The oil solidified on standing.

Analysis: Found: C, 56.46; H, 6.49; N, 16.46.

Calculated for $C_8H_{11}ClN_2$: C, 56.30; H, 6.50; N, 16.42.

EXAMPLE 4

-5-Bromo-2-(1,1-dimethylethyl)pyrimidine

A mixture of 54.5 g of 2-(1,1-dimethylethyl)pyrimidine, 100 g of potassium acetate and 250 ml of glacial acetic acid were heated to gentle reflux and bromine was added dropwise until GLC-analysis (Gas Liquid Chromatographic analysis) showed only traces of starting material. For this 110 g of bromine was needed (theoretical 64 g). The reaction mixture was carefully concentrated under vacuum (reaction product is volatile), the residue dissolved in water and made alkaline by the addition of 20 percent aqueous sodium hydroxide. The product precipitated and was extracted into ether. The ether solution was washed once with saturated sodium chloride solution and dried over anhydrous sodium sulfate. The solvent was removed in a rotary evaporator leaving 83.5 g (97 percent of theoretical) of a white solid. Purity by GLC was 98 percent. Recrystallization from hexane yielded white crystals, m.p. 50°–52° C.

Analysis: Found: C, 44.11; H, 4.92; N, 12.64.

Calculated for $C_8H_{11}BrN_2$: C, 44.67; H, 5.16; N, 13.03.

The compounds 2-cyclopropyl-5-bromo-pyrimidine and 2-isopropyl-5-bromo-pyrimidine are readily prepared as described in Example 3 except for using N-(2-bromo-3-(dimethylamino)-2-propylidene-N-methylmethanaminium perchlorate and the appropriate imidamide as starting materials.

The starting materials used in these reactions are all known compounds; see, for example, U.S. Pat. Nos. 4,012,506 and 3,402,193 and literature sources such as D. J. Brown and R. F. Evans, J. Chem. Soc., 1962, 4039-45; Jutz, Kirchlechner and Seidel, Chem. Ber. 102, 2301-18 (1969); Kucera and Arnold, Collect. Czech. Chem., Commun. 32, 1704-11 (1967) and Oostveen, van der Plas and Jongejan, Rec. Trav. Chim. Pays-Bas 95, 209-11 (1976).

Various modifications may be made in the present invention without departing from the spirit or scope thereof and it is understood that I limit myself only as defined in the appended claims.

I claim:

1. A compound having the formula:

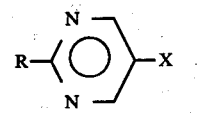

wherein R is cyclopropyl, isopropyl or t-butyl and X is Cl or Br.

2. 5-Chloro-2-cyclopropylpyrimidine.
3. 5-Chloro-2-(1-methylethyl)pyrimidine.
4. 5-Chloro-2-(1,1-dimethylethyl)pyrimidine.
5. 5-Bromo-2-(1,1-dimethylethyl)pyrimidine.